United States Patent
Ivtsenkov et al.

(10) Patent No.: US 8,184,981 B2
(45) Date of Patent: May 22, 2012

(54) SIMPLIFYING AND COST-EFFECTIVE IR-RF COMBAT IDENTIFICATION FRIEND-OR-FOE (IFF) SYSTEM FOR GROUND TARGETS

(75) Inventors: Gennadii Ivtsenkov, Hamilton (CA); Alexandre Mantsvetov, Burlington (CA); Evgeny Berik, Tartu (EE)

(73) Assignee: Protective Arms Systems Inc., Burlington, Ontario (CA)

( * ) Notice: Subject to any disclaimer, the term of this patent is extended or adjusted under 35 U.S.C. 154(b) by 0 days.

(21) Appl. No.: 12/465,715

(22) Filed: May 14, 2009

(65) Prior Publication Data
US 2010/0289691 A1    Nov. 18, 2010

Related U.S. Application Data (60) Provisional application No. 61/061,098, filed on Jun. 12, 2008.

(51) Int. Cl.
*G01S 13/78* (2006.01)
*H04B 10/00* (2006.01)
*H04Q 5/22* (2006.01)

(52) U.S. Cl. ........ 398/115; 398/116; 398/118; 398/123; 398/124; 342/45

(58) Field of Classification Search .......... 398/115–117
See application file for complete search history.

(56) References Cited

U.S. PATENT DOCUMENTS

| | | | |
|---|---|---|---|
| 5,585,953 A * | 12/1996 | Zavrel | 398/115 |
| 5,917,441 A * | 6/1999 | Valentine et al. | 342/20 |
| 5,966,226 A * | 10/1999 | Gerber | 398/108 |
| 7,573,369 B2 * | 8/2009 | Hayles et al. | 340/10.32 |

* cited by examiner

*Primary Examiner* — Danny Leung (57) ABSTRACT

Combined IR-RF combat identification friend-or-foe (IFF) system for a ground targets, such as dismounted soldiers, vehicles or military platforms comprising IR-RF interrogator mounted on a firearm and IR-RF transponder mounted on a friendly target. RF channel operates in Ka-band providing brief information about friendly targets that could be in attacked area, and if they are, develop alert signal: "Friendly soldiers are in the area". The interrogator additionally contains RF channel receiving reflected signal that allows recognize armed foe. IR channel of the system prevents friendly fire in the case of direct sighting to a friendly soldier.

1 Claim, 6 Drawing Sheets

SIMPLIFYING AND COST-EFFECTIVE IR-RF COMBAT IDENTIFICATION FRIEND-OR-FOE (IFF) SYSTEM FOR GROUND TARGETS

CROSS-REFERENCE TO RELATED APPLICATIONS

This application is non-provisional of U.S. Provisional Application No 61/061,098 filed Jun. 12, 2008 by the authors of the present invention. This application relates to the U.S. patent application Ser. Nos. 11/685,682, 12/022,892 and International Patent Application No PCT/CA2007/001846 filed by the authors of the present invention.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.
INCORPORATED-BY-REFERENCE OF MATERIAL SUBMITTED ON A COMPACT DISK
Not Applicable.

FIELD OF THE INVENTION

This invention relates generally to combat identification systems for ground targets and more particularly to a secure covert identification as friend or foe (IFF) system for interrogating a small ground targets, such as military platforms, vehicles and dismounted soldiers that utilizes a coded infrared (IR) and radio (RF) signals received and encoded by the target that sends RF response signal to prevent a friendly fire. It also related to compact RADAR and Rangefinder systems.

DESCRIPTION OF THE RELATED ART

The present invention relates to the U.S. patent application Ser. Nos. 11/685,682, 12/022,892 and International Patent Application No PCT/CA2007/001846 filed by the authors of the present invention.

The Dismounted Armed Forces have an interest in the remote identification of a person as friend or foe, particularly to prevent friendly fire in armed conflicts. Identification as friend or foe (IFF) systems are well-known for decades for military aircraft. Such systems are based on RF transmission and very useful for preventing action against friendly aircrafts.

The military platform commanders target friend-or-foe identification presents a difficult decision for a military platform commander, who must decide whether to engage a detected target while avoiding accidental fratricide.

This problem is even more difficult for the dismounted soldier who may be moving covertly through an unknown combat zone with a limited visibility. U.S. Pat. No. 4,851,849 issued to Otto Albersdoerfer describes a typical active IFF RF technique for a military vehicle, which is equipped with a RF transponder that emits a coded return signal when its receiver detects an interrogating radar pulse.

U.S. Pat. No. 5,686,722 issued to Dobois et al. describes an active optical IFF technique for vehicles uses a selective wavelength optical coding system with tunable optical beacons mounted on each vehicle.

Also, U.S. Pat. No. 5,966,226 issued to Gerber describes an active combat IFF system for a dismounted soldier that includes a weapon-mounted laser transmitter for interrogating suspected targets and a harness including means for receiving the interrogatory signal and means for responding with an encoded radio, acoustic or optical signal.

Therefore, all mentioned and similar IFF systems utilize all-optical, all-radio or combined solutions, where the combined ones use an optical interrogating signal and RF response signal.

Figure 1:
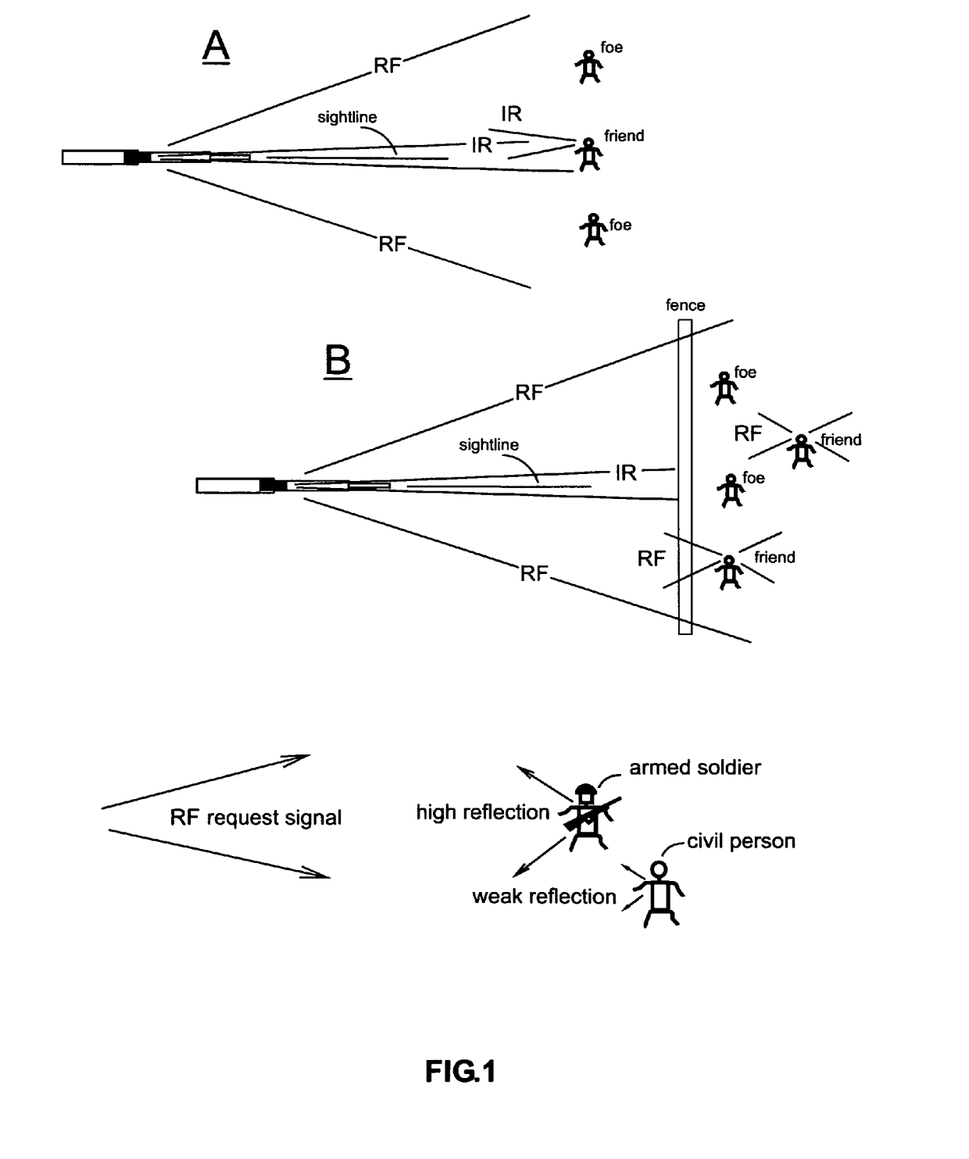
FIG. 1 illustrates cases of operation of IFF system of the preferred embodiment of the present invention in battlefield conditions.

All these systems have obvious disadvantages that could be critical in battlefield conditions. An optical interrogator has a sharp beam profile providing secure covert identification, but can reach the target only when the optical detector mounted on the friendly target is not shaded by any objects, such as leafs, woods, walls, etc. These situations are illustrated on FIG. 1.

Unlike optical signal, RF one passes through the objects, which are not transparent for optical signals, but RF interrogator has very wide diagram because it emits RF signal that has thousands times longer wavelength than optical signal. For example the RF antenna with 30-mm aperture has the transmitting/receiving diagram of 15-20 arc degrees at 8-mm RF wavelength (Ka band). Such wide diagram does not allow recognizing each individual soldier; and the return signal comes from such large area too.

Therefore, only combination of two independent channels, IR optical and RF one, can allow identifying friendly soldiers as in the cases when the sightline is clear as in the case when the sightline is obstructed by some objects. In the last case, a shooter uses RF channel only to get information about a presence of some friendly soldiers in 15-arc degree sector directed along the sightline; it can prevent a chaotic fire that is very often in such situation. In the first case, when the sightline is not obstructed (see FIG. 1), a shooter uses IR optical channel that allows precisely identifying each friendly soldier.

In some cases, both channels may be used, where the RF one provides brief information about possible presence of friendly soldiers is the suspicious sector and, after this IR optical channel is used for final identification.

Therefore, the interrogator of this IFF system has to contain two channels RF and IR ones, which can work simultaneously, but the transponder mounted on a friendly target can contain just a single RF channel There is another very important problem—distinct an armed foe from not-armed civil person. Such person, like an enemy soldier, does not have IFF system and very often can be confused with this soldier; that situation causes heavy civil casualties. Additional small-size receiver incorporated in the interrogator, the object of the present invention, can solve this problem.

SUMMARY OF THE INVENTION

The present invention is based on the art described in the U.S. patent application Ser. Nos. 11/685,682, 12/022,892 and solves the mentioned above problems by providing a combined IR-RF system, which can be used in both combat situations: when the sightline is not shaded and when the sightline is obstructed. IFF system of the present invention also allows to distinct armed soldier from non-armed person. Here, IFF interrogator has combined RF/IR transmitter/receiver additionally equipped with another RF receiver that receives and processes RF signal reflected from a target; whereas the IFF transponder has single RF transmitter/receiver. Another embodiment of the present invention allows disarming friendly aircraft bombs and missiles.

DETAILED DESCRIPTION OF THE PREFERRED EMBODIMENTS OF THE INVENTION—IR-RF COMBINED IFF SYSTEM

Figure 2:
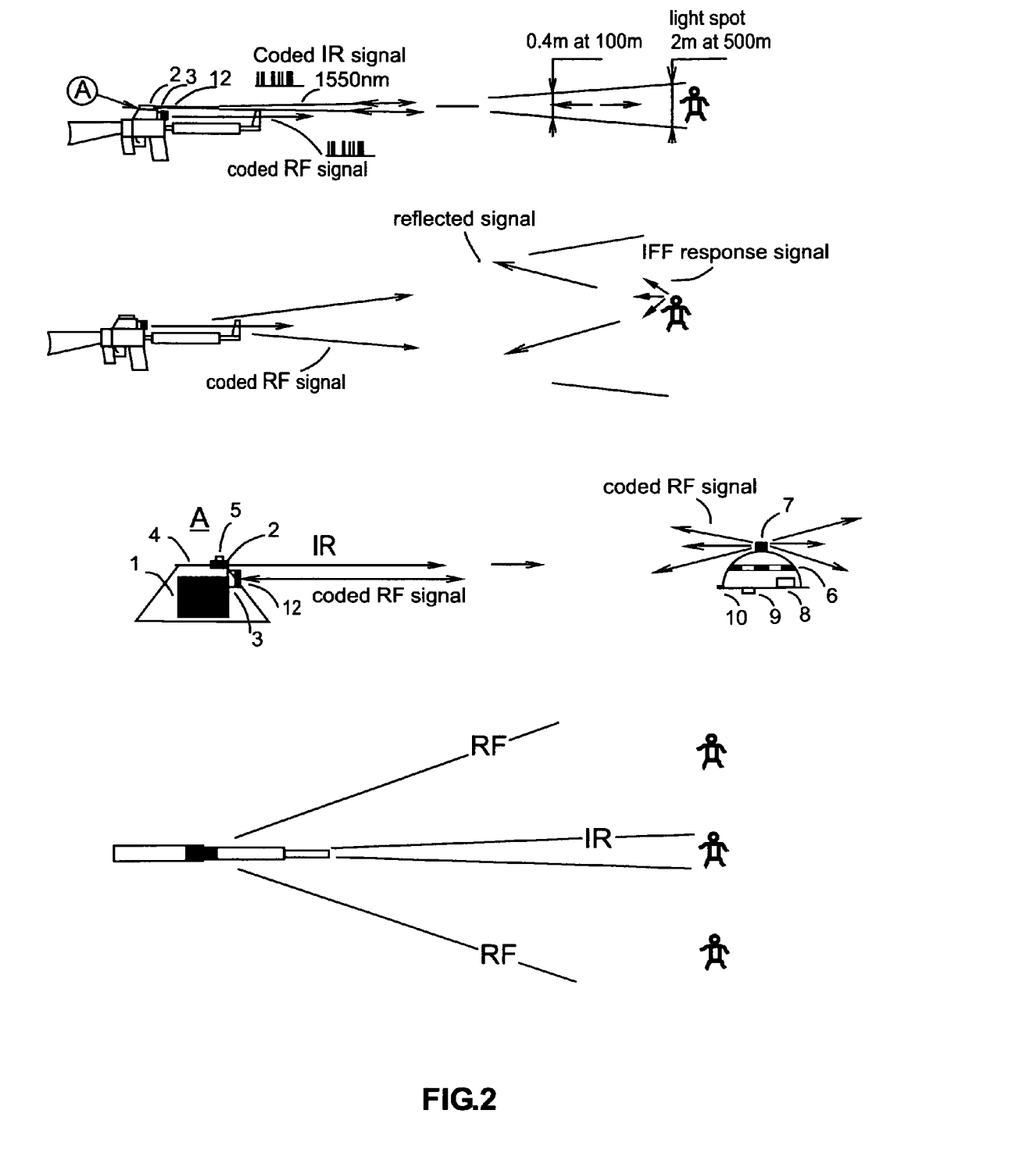
FIG. 2 depicts the schematic diagram of IFF system of the preferred embodiment.

The schematic diagram of IFF system of the present invention is depicted in FIG. 2. The IFF system—the object of the present invention—includes a weapon-mounted RF/IR interrogatory unit and response (transponder) unit sending RF return signal when it is activated by coded RF or/and IR signal of the interrogator. Radio (RF) units, which contains RF transmitter and receiver, are installed in both—the interrogator and transponder—so providing two-way RF signal exchange, whereas IR channel of the interrogator contains IR transmitter only; and the transponder is equipped with a wide-diagram optical receiver only. It means that IR channel works in one direction sending encoded optical signal from the interrogator to the transponder. Such solution allows significantly simplifying response (transponder) unit. In many cases such architecture can be good enough, especially in the case when enemy troops are not equipped with sophisticated RF jamming and detecting devices. The system of the present invention is flexible and, if it necessary, allows installing optical units on interrogatory and response (transponder) units so providing full IR-RF combination described in U.S. patent application Ser. No. 12/022,892.

The system also equipped with additional RF receiving channel installed in the interrogator. This RF channel is tuned to the same wavelength as RF transmitter of the interrogator. It receives RF signal reflected from the target. If the target is a soldier equipped with firearm, such as rifle, propelled grenade launcher, etc., the reflected from metal object signal is much stronger than one reflected from non-metal object. Therefore, this additional RF channel together with RF transmitter of the interrogator work as a short-distance RADAR and rangefinder providing information about number of target and distances; and, being calibrated, it can recognize an armed soldier. This information can avoid civil causalities.

The RF channel of IFF system—the object of the present invention—utilizes the short-wavelength (Ka band) RF signal that allows emitting RF signal in a relatively narrow (for small 30-mm-aperture antenna) sector of 15-20 arc degrees directed along the sightline of the firearm. The hardware of Ka-band RF channel is well developed, has a small size and weight, and inexpensive.

The request unit (interrogator) contains the IR transmitting optical unit equipped with short fiber-optic line 4 and lens 2, RF transmitting/receiving antenna 3, additional RF receiving antenna 12, electronic block 1 and alert light 5.

The response unit (transponder) contains unidirectional optical receiver 6, unidirectional RF receiving/transmitting antenna 7, electronic block 8, alert buzzer 9 and light 10.

Detailed Description of RF Channel of the Request Unit (Interrogator)

Figure 3:
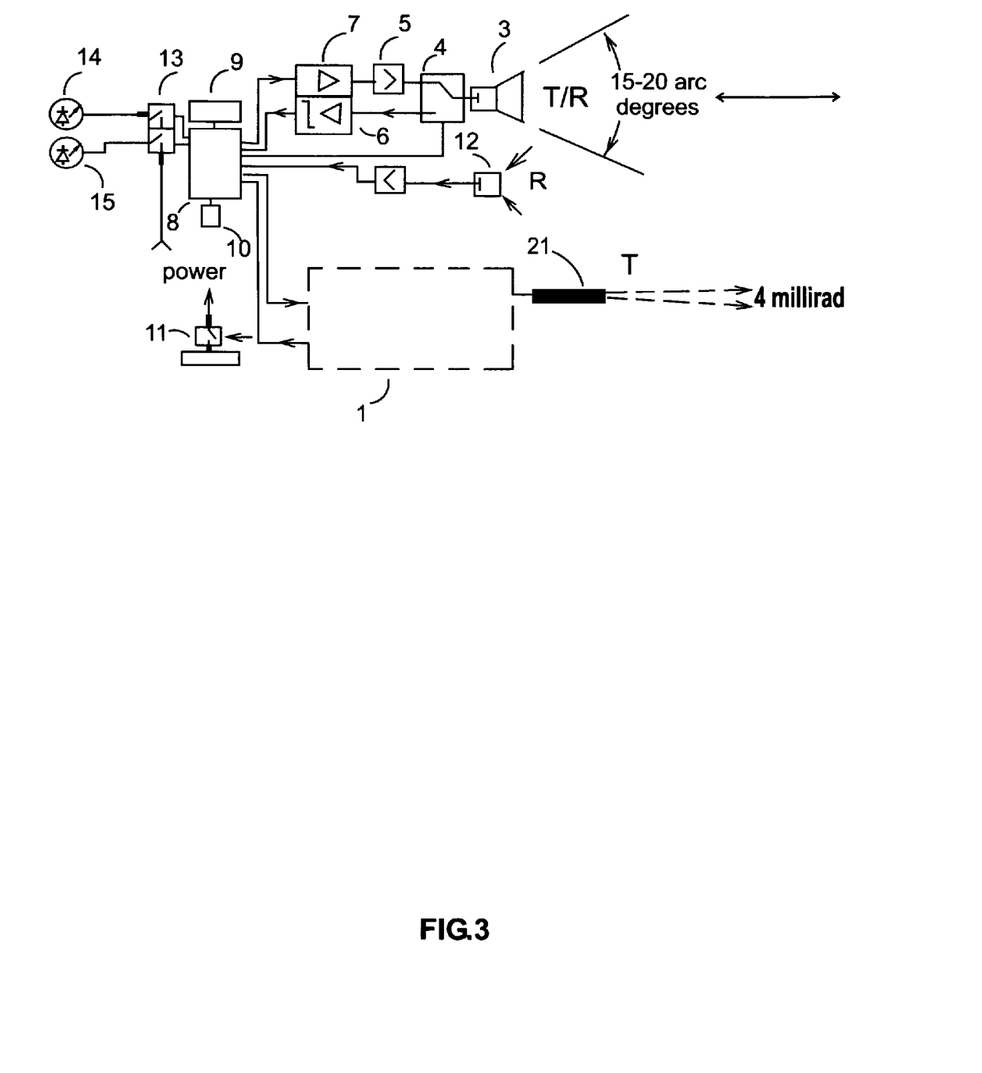
FIG. 3 depicts the block diagram of the RF interrogator of the preferred embodiment.

The detailed block diagram of interrogator is depicted in FIG. 3. The single electronic block, which is common for both—IR and RF—channels, contains microprocessor 8, flush memory 9, USB port 10, alert LED 14 and switch 13. It develops coded request signals, decodes input response signal and activates alert LED 14. Also, it processes reflected RF signal received by antenna 12 to find whether the target is an armed soldier. The electronic block develops 3 following alert signals that activate LED 14 and 15: "friend(s) in 15-degree sector", "armed foe in 15-degree sector" and "friend is targeted, don't shoot". To separate these signals, the LED 14 and 15 can blink, or change color.

IR channel 1 of the interrogator is similar to one described in U.S. patent application Ser. No. 12/022,892.

The RF channel uses the RF transponder, which consists of one transmitting and two receiving channels. The transmitting channel contains RF switch 4 that switches transponder modes between "transmitting" and "receiving" ones. That solution allows using a single antenna 3 and separate response signal coming from the transponder from RF signal reflected from any object. The transmitting channel contains pre-amplifier-modulator 7 and power amplifier 5 feeding antenna 3 in "transmitting" mode. The receiving channel contains detector-amplifier-former 6 that detects (demodulates), amplifies and forms shape of digital RF signals coming from transmitting/receiving antenna 3 in "receiving" mode. Pre-amplifier-modulator 7 modulates and amplifies the digital electric signals developed by processor 8. Power amplifier 5 provides necessary power of output signal that is transmitted to the response unit by antenna 3. Received by antenna 3 RF response signal is demodulated and pre-amplified by detector-amplifier-former 16 that, also, standardizes digital output signal entering processor 8. The switch 4 is controlled by processor 8.

The antenna 12 of the interrogator receives RF signal reflected from objects situated in 15-degree sector along the sightline. These objects can be immobile natural ones, such as trees, etc., or mobile persons, wherein some of them can be armed. Because reflection of armed person in RF waveband higher than reflection from non-armed one the electronic unit of the interrogator can identify armed person so informing the shooter about. For this, processor 8 calculates distance to the reflecting object using time shift between transmitted and received signals, compares ratio of the signals with one written in memory 9 and makes decision about reflected object—whether it is an armed soldier, or not. It means that the interrogator develops signal: "armed foe in 15-degree sector". Here, the additional RF receiver (antenna 12) together with transmitting channel of the interrogator works as short-range RADAR.

RF transponder of the present invention utilizes Ka-waveband. The hardware of this waveband is well-developed (particularly, for satellite communication) and inexpensive.

Figure 4:
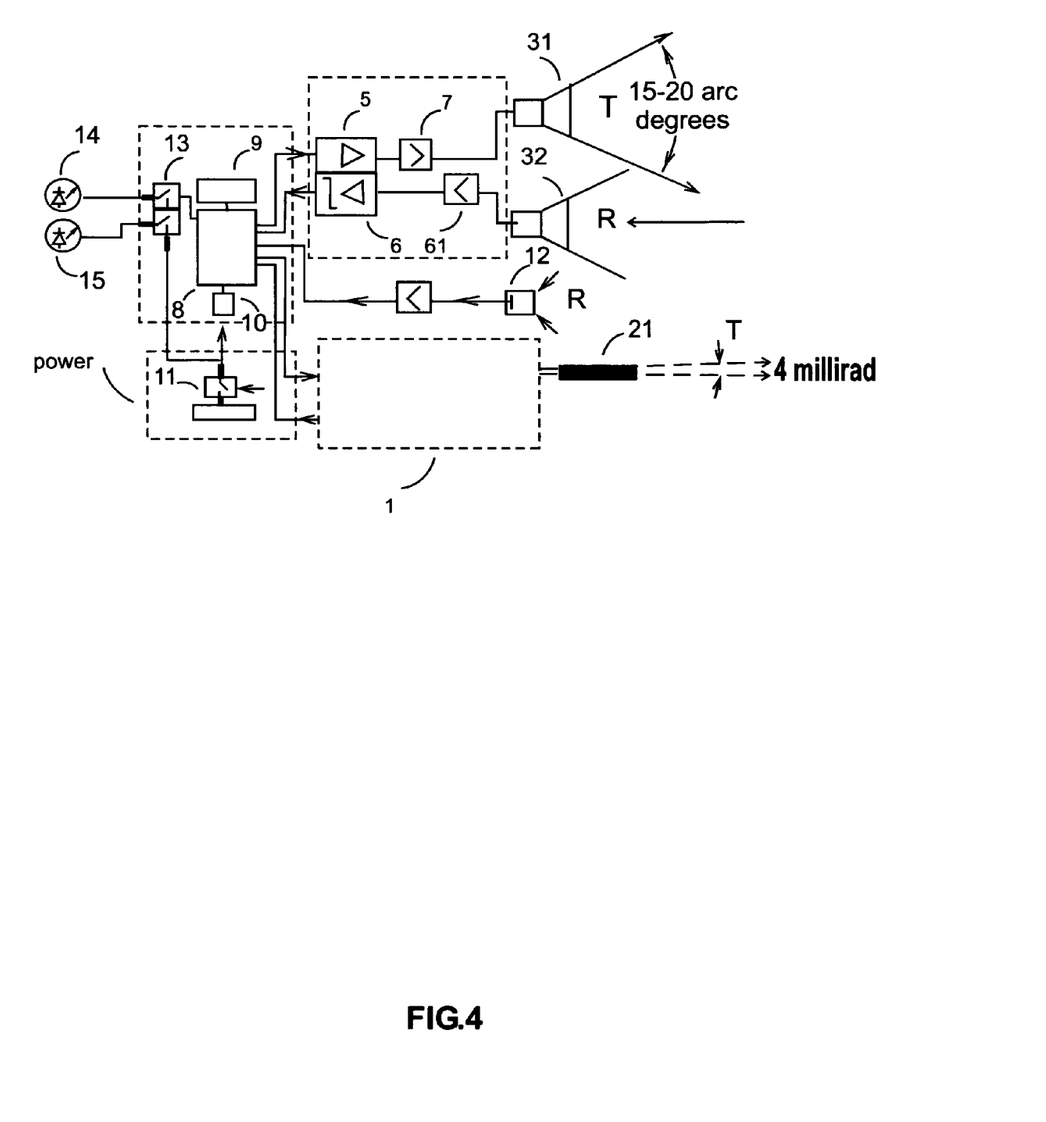
FIG. 4 depicts the block diagram of another embodiment of the RF interrogator.

Another variant of interrogator embodiment providing duplex communication is depicted in FIG. 4. Here, the transmitter and receiver have separate antennas 31 and 32. To achieve duplex communication between interrogator and transponder, frequencies of transmitting and receiving signals are shifted. Interrogator of this embodiment comprises additional elements, but it allows making signal exchange between the interrogator and transponder faster. The interrogator of this embodiment utilizes the same elements that were utilized in the previous embodiment, except antennas 31 and 32 and pre-amplifier 61 that amplifies incoming RF signal. The RF channel receiving reflected signal is the similar to one of the previous embodiment.

Detailed Description of RF Channel of the Response Unit (Transponder)

Figure 5:
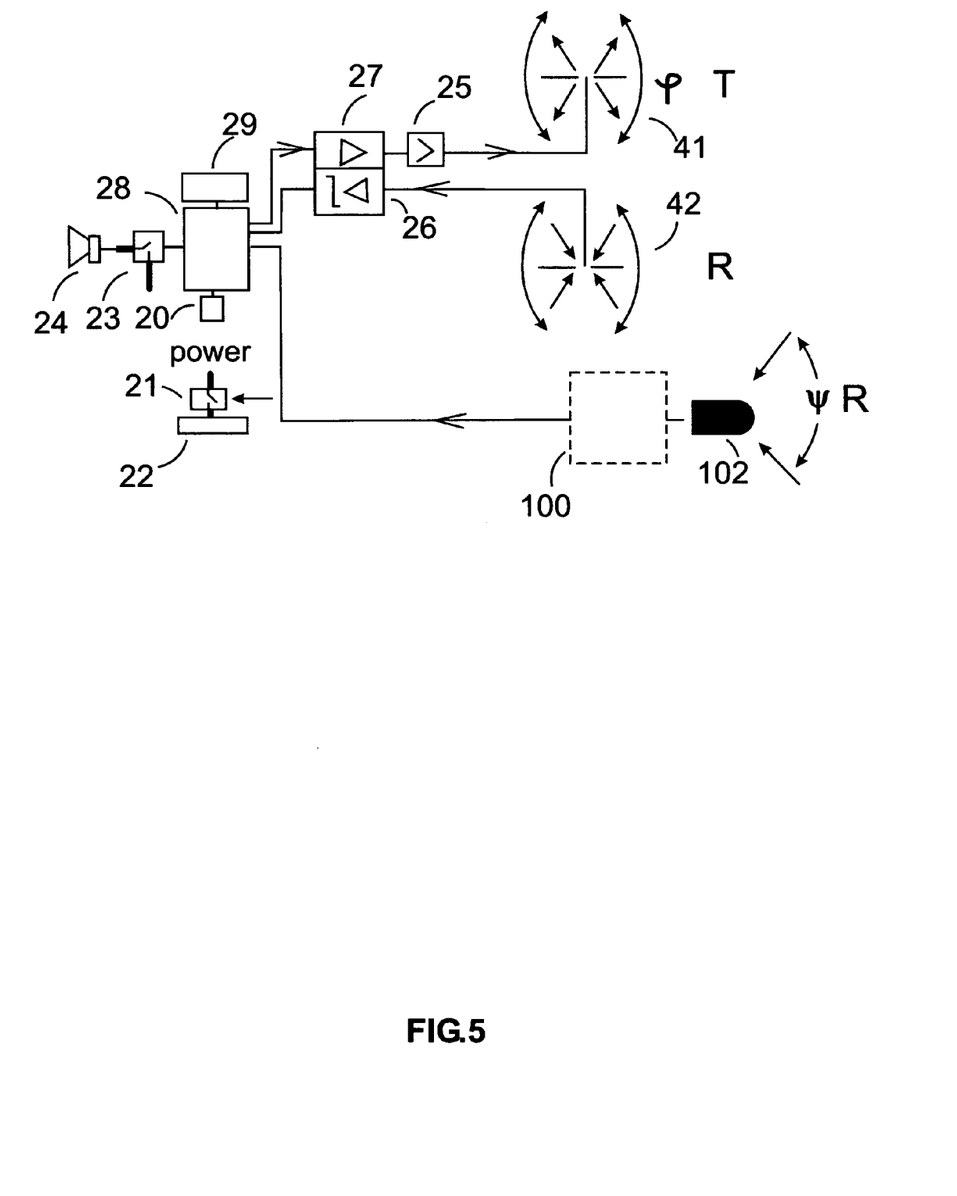
FIG. 5 depicts the block diagram of the RF transponder of the preferred embodiment.

The detailed block diagram of RF channel of the response unit is depicted in FIG. 5.

The RF channel of the transponder contains the blocks that are similar to the ones of the interrogator depicted in FIG. 4. Unlike RF channel of the interrogator, the RF channel of the transponder comprises two antennas—transmitting 41 and receiving 42, wherein these antennas have wide unidirectional diagram that covers hemisphere so providing single response for all request signals coming from any direction.

The response unit contains single electronic block 21, consisting of microprocessor 28, flush memory 29, USB port 20, alert buzzer 24, and switch 23. It processes an input request signal coming from RF and/or IR receivers, activates alert buzzer 24, and develops coded RF request signals. To separate the alert signals coming from IR and RF channels, the buzzer 24 can sound by short signals if it is activated by the RF signal, or change tone of the sound, for example.

The transmitting RF channel of the transponder contains the pre-amplifier-modulator 27 and power amplifier 25 feeding antenna 41. The pre-amplifier-modulator 27 modulates and amplifies the digital electric signals developed by processor 28. The power amplifier 25 provides necessary power of output signal that is transmitted to the response unit via antenna 41.

The receiving RF channel of the transponder contains detector-amplifier-former 26 that detects (demodulates), amplifies and fixes shape of digital RF signals coming from receiving antenna 42. Received by antenna 42 RF response signal is demodulated and pre-amplified by the detector-amplifier-former 26 that, also, standardizes the digital output signal entering processor 28.

To prevent a false alert, the request and response signals utilize different frequencies, wherein the responsive Ka-band RF signal emitted by the transponder is in compliance with STANAG4579 standard. Such solution additionally allows monitoring battlefield situation. Also, the request and response signals are shifted in time in such a way when the response signal is delayed against the request one for a specific time—a portion of millisecond. It means that the interrogator of the first embodiment (FIG. 3) switches to the receiving channel only after this specific time and holds it on for a short time period of a portion of millisecond—the time that is necessary to receive the response signal. Thus, it allows the system rejecting the RF signals coming from other sources. The interrogator of the second embodiment (FIG. 4), which does not have RF switch, can switch the channel logically closing input of the processor (position 8 on FIG. 4).

Therefore, the system works as follows:

The interrogator sends encoded RF signal towards the area to which the sightline is directed. It activates the response units of friendly targets that are in this area.

The response unit sends with certain fixed time delay an encoded response RF signal, which when received by the request unit of the shooter gives him an alert signal: "friendly targets in 15-degree sector". Also, the interrogator receives RF signals reflected from this area, and, if armed persons are in the area that do not send response signal, the electronic unit of the interrogator developed alert signal "armed foe in 15-degree sector". In the case when both—friendly and enemy soldiers—appear in this area, the electronic unit of the transponder calculates number of response signals an compare it with the number of detected armed persons; so it developed both alert signals—"friendly targets in 15-degree sector" and "armed foe in 15-degree sector".

This signal activates IR receiver of the transponder; and, when sharp IR signal sent by the interrogator reaches optical sensor mounted on friendly soldiers, RF unit of the transponder sends second encoded radio response which means "friend is targeted, do not shoot!". This RF signal received by request unit prevents a friendly fire.

Figure 6:
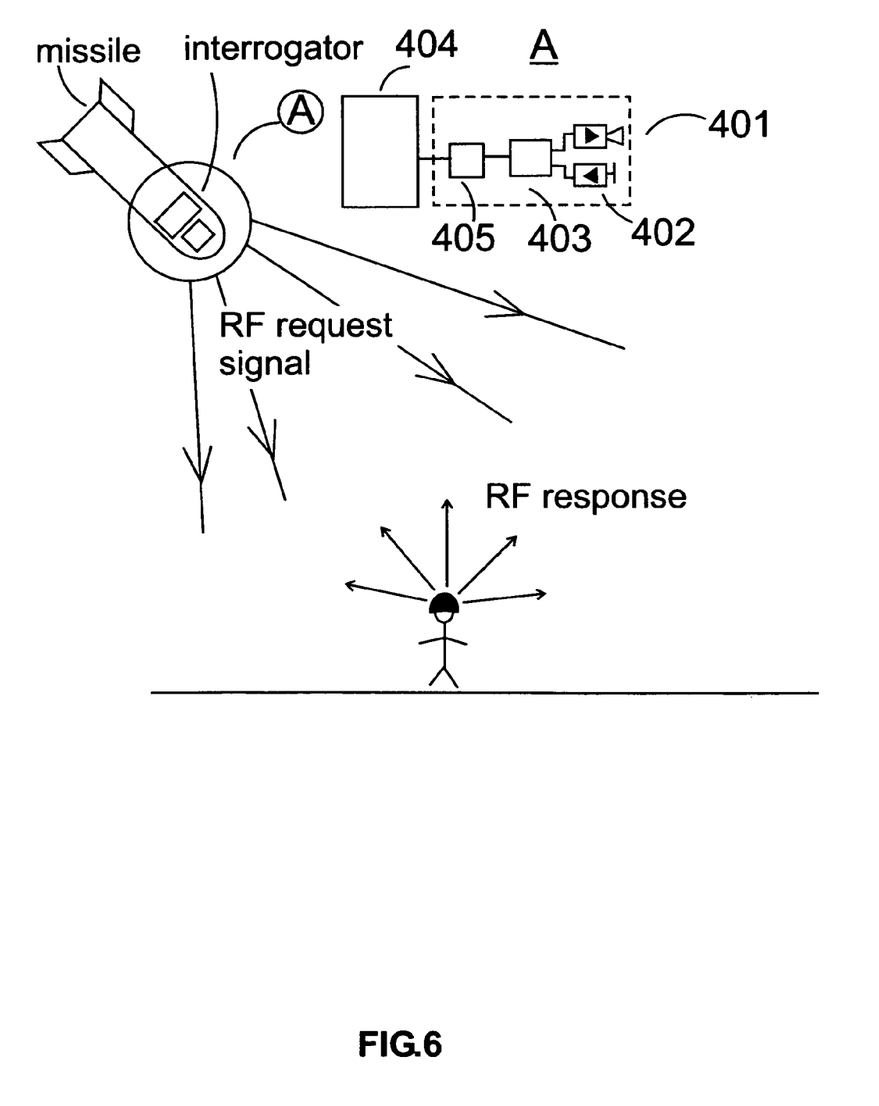
FIG. 6 depicts the schematic diagram of IFF system for disarming friendly aircraft bombs and missiles.

Detailed Description of the Another Embodiments of the Invention—IFF System For Bomb and Missile Disarming The modification of RF channel of IFF system of the preferred embodiment can be utilized to disarm aircraft bomb, artillery shells and directed missiles mistakenly targeting friendly targets. In this case the RF response unit (transponder) of an individual soldier stills the same that is utilized in the preferred embodiment; only interrogator is modified. The interrogator of this embodiment is installed on a bomb or missile as depicted in FIG. 6. It contains power supply 404, Ka-band RF transmitter 401, RF receiver 402, electronic logical unit 403, electronic disarming system 405 that communicates with bomb's fuse and allows preventing the bomb explosion. The directional diagram of the RF transmitter 1 of said interrogator is relatively wide—about 60 arc degrees; and it is directed along missile's axis. The interrogator starts working immediately after the missile launching. The range of the interrogator is restricted up to hundred meters; therefore, such range together with antenna directivity allows communicate only with targets located in the possible destruction zone of said missile. So, when the missile is approaching the target the transponder of the IFF system receives the encoded signal emitted by the interrogator. The transponder of the IFF system recognizes the signal and sends encoded response. The RF receiver of the interrogator recognizes the signal and sends the disarming signal the bomb's fuse. The bomb falls on a ground, but it does not explode. Because the range of the IFF system of this embodiment is restricted by hundred meters, the time of signal exchanging, processing and disarming is limited by 300 milliseconds for subsonic missiles and about 100 milliseconds—for supersonic ones. The interrogator of IFF system of this embodiment contains high-speed electronics that allows disarming the bomb in tens milliseconds—before the bomb falls on the ground.

IFF system of this embodiment can be utilizes in "smart missiles" that equipped with electronics and electrical fuse. The power supply 404 of the transponder can be common for all onboard electronic equipment. It can be any kind of electrical battery or, preferably, it can be power supply based on Inertial Accumulator that is described in U.S. patent application Ser. No 12/392,561. Such power supply is energized by projectile rotation or axial acceleration. It does not require any batteries and start working immediately after launching.

What is claimed is:

1. An identification friend or foe system for military firearms and ground targets to determine whether a target that has been selected is a friendly target comprising:

an interrogator attached to said firearm and containing IR signal source arranged to radiate encrypted request signals, a RF detection system that receives a RF response signal and a visual alert sign that is activated by said received response signal, a transponder containing IR detection system attached to a friendly target that receives said IR request signal, a RF signal source attached to a friendly target and arranged to radiate said RF response signals, and a sound alert buzzer mounted on said friendly target and activated by said received request signal, wherein the improvement comprises:

said interrogator additionally having a RF transmitter, which sends encrypted RF request signal in area to which sightline of said firearm is directed, and a single electronic unit mounted in convenient place of the firearm, which contains transmitting and receiving electronic channels and a microprocessor that controls IR and RF channels of said interrogator, wherein said transmitting and receiving electronic channels are connected to said microprocessor that develops coded request signal, processes input response signals and activates said visual alert sign, said transponder additionally having RF receiver, which receives encrypted RF request signal emitted by said interrogator, and a single electronic unit mounted in convenient place of said friendly target, which contains transmitting and receiving electronic channels and a microprocessor that controls IR and RF channels of said transponder, wherein said transmitting and receiving electronic channels are connected to said microprocessor that develops coded response signal, processes input request signals and activates said sound alert buzzer, wherein the interrogator additionally comprises:

a. a second receiving RF antenna and a second receiving RF channel, wherein said second receiving RF antenna is connected to said second receiving RF channel that is tuned on the same frequency as the transmitting RF channel; therefore, said second receiving RF channel receives RF signal reflected from objects appearing in the area to, which sightline of said firearm is directed, wherein said reflected signal is significantly higher for targets having metal objects, b. the microprocessor that has additional ability processing said reflected RF signal to determine distance to said objects and its reflectivity; therefore, said processor collects information about distance and reflectivity of possible target that together with information about friendly target in said area allows said processor recognizing not only a friendly target, but also an armed foe.

* * * * *